United States Patent [19]

Bundy

[11] 4,159,385
[45] Jun. 26, 1979

[54] 9-DEOXY-9-METHYLENE-5-OXA-16-PHENYL-PGF$_1$ COMPOUNDS

[75] Inventor: Gordon L. Bundy, Portage, Mich.

[73] Assignee: The Upjohn Company, Kalamazoo, Mich.

[21] Appl. No.: 923,833

[22] Filed: Jul. 12, 1978

Related U.S. Application Data

[63] Continuation-in-part of Ser. No. 786,249, Apr. 11, 1977, Pat. No. 4,118,584.

[51] Int. Cl.$^2$ .......................................... C07C 177/00
[52] U.S. Cl. ...................................... 560/55; 562/465; 562/470; 560/60
[58] Field of Search .................... 560/55, 60; 562/470, 562/465

*Primary Examiner*—Paul J. Killos
*Attorney, Agent, or Firm*—Robert A. Armitage

[57] ABSTRACT

The present invention relates to novel 9-deoxy-9-methylene-5-oxa-16-phenyl-PGF$_1$ compounds. These compounds are useful pharmacological agents, and are useful for the same purposes as the corresponding PGE-type compounds.

99 Claims, No Drawings

9-DEOXY-9-METHYLENE-5-OXA-16-PHENYL-PGF₁ COMPOUNDS

CROSS REFERENCE TO RELATED APPLICATIONS

This application is a continuation-in-part of Ser. No. 786,249, filed Apr. 11, 1977, now issued as U.S. Pat. No. 4,118,584.

The present invention relates to novel 9-deoxy-9-methylene-5-oxa-16-phenyl-PGF₁ compounds, the essential material constituting a disclosure of which is incorporated here by reference from U.S. Pat. No. 4,118,584.

I claim:

1. A prostaglandin analog of the formula

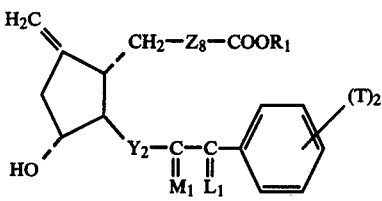

wherein $Y_2$ is trans-CH=CH— or —CH₂CH₂—;
wherein $M_1$ is

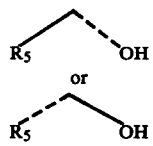

or

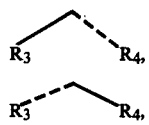

wherein $R_5$ is hydrogen or methyl;
wherein $L_1$ is

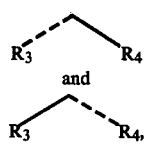

or a mixture of

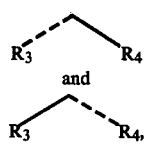

wherein $R_3$ and $R_4$ are hydrogen, methyl, or fluoro, being the same or different, with the proviso that one of $R_3$ and $R_4$ is fluoro only when the other is hydrogen or fluoro;
wherein $Z_8$ is —CH₂—O—CH₂—(CH₂)$_g$—CH₂—
wherein g is one, 2, or 3; wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl;
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation, and the 1,11- or 1,15-lactones thereof.

2. A prostaglandin analog according to claim 1, wherein $Y_2$ is —CH₂CH₂—.

3. A prostaglandin analog according to claim 2, whrein $M_1$ is

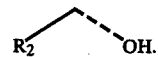

4. A prostaglandin analog according to claim 3, wherein s is zero or one and T is chloro, fluoro, or trifluoromethyl.

5. A prostaglandin analog according to claim 4, wherein g is 3.

6. 9-Deoxy-9-methylene-2a,2b-dihomo-15-methyl-16-phenyl-17,18,19,20-tetranor-13,14-dihydro-PGF₁, a prostaglandin analog according to claim 5.

7. 9-Deoxy-9-methylene-2a,2b-dihomo-16-phenyl-17,18,19,20-tetranor-13,14-dihydro-PGF₁, a prostaglandin analog according to claim 5.

8. A prostaglandin analog according to claim 2, wherein $M_1$ is

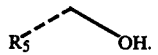

9. A prostaglandin analog according to claim 8, wherein s is zero or one and T is chloro, fluoro, or trifluoromethyl.

10. A prostaglandin analog according to claim 9, wherein g is 3.

11. 9-Deoxy-9-methylene-2a,2b-dihomo-15-epi-15-methyl-16-phenyl-17,18,19,20-tetranor-13,14-dihydro-5-oxa-PGF₁, a prostaglandin analog according to claim 10.

12. 9-Deoxy-9-methylene-2a,2b-dihomo-15-epi-16-phenyl-17,18,19,20-tetranor-13,14-dihydro-5-oxa-PGF₁, a prostaglandin analog according to claim 10.

13. A prostaglandin analog according to claim 9, whrein g is 1.

14. A prostaglandin analog according to claim 13, wherein at least one of $R_3$ and $R_4$ is methyl.

15. 9-Deoxy-9-methylene-15-epi-16-methyl-phenyl-18,19,20-trinor-13,14-dihydro-5-oxa-PFG₁, a prostaglandin analog according to claim 14.

16. A prostaglandin analog according to claim 13, wherein at least one of $R_3$ and $R_4$ is fluoro.

17. 9-Deoxy-9-methylene-15-epi-16,16-difluoro-16-phenyl-17,18,19,20-tetranor-13,14-dihydro-5-oxa-PGF₁, a prostaglandin analog according to claim 16.

18. A prostaglandin analog according to claim 13, wherein $R_3$ and $R_4$ are both hydrogen.

19. 9-Deoxy-9-methylene-15-epi-16-methyl-16-phenyl-17,18,19,20-tetranor-13,14-dihydro-5-oxa-PGF₁, a prostaglandin analog according to claim 18.

20. A prostaglandin analog according to claim 2, wherein $M_1$ is

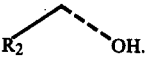

21. A prostaglandin analog according to claim 20, wherein s is zero or one and T is chloro, fluoro, or trifluoromethyl.

22. A prostaglandin analog according to claim 21, wherein g is 3.

23. A prostaglandin analog according to claim 22, wherein at least one of $R_3$ and $R_4$ is methyl.

24. 9-Deoxy-9-methylene-2a,2b-dihomo-16-methyl-16-phenyl-18,19,20-trinor-13,14-dihydro-5-oxa-PGF$_1$, a prostaglandin analog according to claim 23.

25. A prostaglandin analog according to claim 22, wherein at least one of $R_3$ and $R_4$ is fluoro.

26. 9-Deoxy-9-methylene-2a,2b-dihomo-16,16-difluoro-16-phenyl-17,18,19,20-tetranor-13,14-dihydro-5-oxa-PGF$_1$, a prostaglandin analog according to claim 25.

27. A prostaglandin analog according to claim 22, wherein $R_3$ and $R_4$ are both hydrogen.

28. 9-Deoxy-9-methylene-2a,2b-dihomo-16-phenyl-17,18,19,20-tetranor-13,14-dihydro-5-oxa-PGF$_1$, a prostaglandin analog according to claim 27.

29. A prostaglandin analog according to claim 11, wherein g is 1.

30. A prostaglandin analog according to claim 29, wherein at least one of $R_3$ and $R_4$ is methyl.

31. A prostaglandin analog according to claim 30, wherein $R_3$ and $R_4$ are both methyl.

32. 9-Deoxy-9-methylene-16-methyl-16-phenyl-18,19,20-trinor-13,14-dihydro-5-oxa-PGF$_1$, tris-(hydroxymethyl)aminomethane salt, a prostaglandin analog according to claim 31.

33. 9-Deoxy-9-methylene-16-methyl-16-phenyl-18,19,20-trinor-13,14-dihydro-5-oxa-PGF$_1$, methyl ester, a prostaglandin analog according to claim 31.

34. 9-Deoxy-9-methylene-16-methyl-16-phenyl-18,19,20-trinor-13,14-dihydro-5-oxa-PGF$_1$, methyl ester, a prostaglandin analog according to claim 31.

35. A prostaglandin analog according to claim 29, wherein at least one of $R_3$ and $R_4$ is fluoro.

36. A prostaglandin analog according to claim 35, wherein $R_3$ and $R_4$ are both fluoro.

37. A prostaglandin analog according to claim 36, wherein $R_5$ is methyl.

38. 9-Deoxy-9-methylene-15-methyl-16,16-difluoro-16-phenyl-17,18,19,20-tetranor-13,14-dihydro-5-oxa-PGF$_1$, a prostaglandin analog according to claim 37.

39. A prostaglandin analog according to claim 36, wherein $R_5$ is hydrogen.

40. 9-Deoxy-9-methylene-16,16-difluoro-16-phenyl-17,18,19,20-tetranor-13,14-dihydro-5-oxa-PGF$_1$, a prostaglandin analog according to claim 39.

41. A prostaglandin analog according to claim 29, wherein $R_3$ and $R_4$ are both hydrogen.

42. A prostaglandin analog according to claim 41, wherein $R_5$ is methyl.

43. 9-Deoxy-9-methylene-15-methyl-16-phenyl-17,18,19,20-tetranor-13,14-dihydro-5-oxa-PGF$_1$, tris-(hydroxymethyl)aminomethane salt, a prostaglandin analog according to claim 42.

44. 9-Deoxy-9-methylene-15-methyl-16-phenyl-17,18,19,20-tetranor-13,14-dihydro-5-oxa-PGF$_1$, methyl ester, a prostaglandin analog according to claim 42.

45. 9-Deoxy-9-methylene-15-methyl-16-phenyl-17,18,19,20-tetranor-13,14-dihydro-5-oxa-PGF$_1$, a prostaglandin analog according to claim 42.

46. A prostaglandin analog according to claim 41, wherein $R_5$ is hydrogen.

47. 9-Deoxy-9-methylene-16-phenyl-17,18,19,20-tetranor-13,14-dihydro-5-oxa-PGF$_1$, methyl ester, a prostaglandin analog according to claim 46.

48. 9-Deoxy-9methylene-16-phenyl-17,18,19,20-tetranor-13,14-dihydro-5-oxa-PGF$_1$, a prostaglandin analog according to claim 46.

49. A prostaglandin analog according to claim 1, wherein $Y_2$ is trans-CH=CH—.

50. 9-Deoxy-9-methylene-16-methyl-16-phenyl-18,19,20-trinor-PGF$_1$, a prostaglandin analog according to claim 49.

51. A prostaglandin analog according to claim 49, wherein at least one of $R_3$ and $R_4$ is fluoro.

52. A prostaglandin analog according to claim 51, wherein $R_3$ and $R_4$ are both fluoro.

53. 9-Deoxy-9-methylene-16,16-difluoro-16-phenyl-17,18,19,20-tetranor-PGF$_1$, a prostaglandin analog according to claim 52.

54. A prostaglandin analog according to claim 49, wherein $R_3$ and $R_4$ are both hydrogen.

55. A prostaglandin analog according to claim 54, wherein $R_5$ is methyl.

56. 9-Deoxy-9-methylene-15-methyl-16-phenyl-17,18,19,20-tetranor-PGF$_1$, a prostaglandin analog according to claim 55.

57. A prostaglandin analog according to claim 54, wherein $R_5$ is hydrogen.

58. 9-Deoxy-9-methylene-16-phenyl-17,18,19,20-tetranor-PGF$_1$, a prostaglandin analog according to claim 57.

59. A prostaglandin analog according to claim 49, wherein $M_1$ is

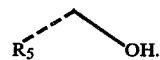

60. A prostaglandin analog according to claim 59, wherein s is zero or one and T is chloro, fluoro, or trifluoromethyl.

61. A prostaglandin analog according to claim 60, wherein g is 3.

62. 9-Deoxy-9-methylene-2a,2b-dihomo-15-epi-15-methyl-16-phenyl-17,18,19,20-tetranor-5-oxa-PGF$_1$, a prostaglandin analog according to claim 61.

63. 9-Deoxy-9-methylene-2a,2b-dihomo-15-epi-16-phenyl-17,18,19,20-tetranor-5-oxa-PGF$_1$, a prostaglandin analog according to claim 61.

64. A prostaglandin analog according to claim 60, wherein g is 1.

65. A prostaglandin analog according to claim 64, wherein at least one of $R_3$ and $R_4$ is methyl.

66. 9-Deoxy-9-methylene-15-epi-16-methyl-16-phenyl-18,19,20-trinor-5-oxa-PGF$_1$, a prostaglandin analog according to claim 65.

67. A prostaglandin analog according to claim 64, wherein at least one of $R_3$ $R_4$ is fluoro.

68. 9-Deoxy-9-methylene-15-epi-16,16-difluoro-16-phenyl-17,18,19,20-tetranor-5-oxa-PGF$_1$, a prostaglandin analog according to claim 67.

69. A prostaglandin analog according to claim 64, wherein $R_3$ and $R_4$ are both hydrogen.

70. 9-Deoxy-9-methylene-15-epi-15-methyl-16-phenyl-17,18,19,20-tetranor-5-oxa-PGF$_1$, a prostaglandin analog according to claim 69.

71. A prostaglandin analog according to claim 49, wherein $M_1$ is

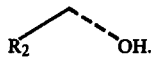

72. A prostaglandin analog according to claim 71, wherein s is zero or one and T is chloro, fluoro, or trifluoromethyl.

73. A prostaglandin analog according to claim 72, wherein g is 3.

74. A prostaglandin analog according to claim 73, wherein at least one of $R_3$ and $R_4$ is methyl.

75. 9-Deoxy-9-methylene-2a,2b-dihomo-16-methyl-16-phenyl-18,19,20-trinor-5-oxa-$PGF_1$, a prostaglandin analog according to claim 74.

76. A prostaglandin analog according to claim 73, wherein at least one or $R_3$ and $R_4$ is fluoro.

77. 9-Deoxy-9-methylene-2a,2b-dihomo-16,16-difluoro-16-phenyl-17,18,19,20-tetranor-5-oxa-$PGF_1$, a prostaglandin analog according to claim 74.

78. A prostaglandin analog according to claim 73, wherein $R_3$ and $R_4$ are both hydrogen.

79. 9-Deoxy-9-methylene-2a,2b-dihomo-15-methyl-16-phenyl-17,18,19,20-tetranor-5-oxa-$PGF_1$, a prostaglandin analog according to claim 78.

80. A prostaglandin analog according to claim 72, wherein g is 1.

81. A prostaglandin analog according to claim 80, wherein at least one of $R_3$ and $R_4$ is methyl.

82. A prostaglandin analog according to claim 81, wherein $R_3$ and $R_4$ are both methyl.

83. 9-Deoxy-9-methylene-16-phenyl-18, 19, 20-trinor-5-oxa-$PGF_1$, tris(hydroxymethyl)aminomethane salt, a prostaglandin analog according to claim 82.

84. 9-Deoxy-9-methylene-16-methyl-16-phenyl-18,19,20-trinor-5-oxa-$PGF_1$, methyl ester, a prostaglandin analog according to claim 82.

85. 9-Deoxy-9-methylene-16-methyl-16-phenyl-18,19,20-trinor-5-oxa-$PGF_1$, a prostaglandin analog according to claim 82.

86. A prostaglandin analog according to claim 80, wherein at least one of $R_3$ $R_4$ is fluoro.

87. A prostaglandin analog according to claim 86, wherein $R_3$ and $R_4$ are both fluoro.

88. A prostaglandin analog according to claim 87, wherein $R_5$ is methyl.

89. 9-Deoxy-9-methylene-15-methyl-16,16-difluoro-16-phenyl-17,18,19,20-tetranor-5-oxa-$PGF_1$, a prostaglandin analog according to claim 88.

90. A prostaglandin analog according to claim 87, wherein $R_5$ is hydrogen.

91. 9-Deoxy-9-methylene-16,16-difluoro-16-phenyl-17,18,19,20-tetranor-5-oxa-$PGF_1$, a prostaglandin analog according to claim 90.

92. A prostaglandin analog according to claim 90, wherein $R_3$ and $R_4$ are both hydrogen.

93. A prostaglandin analog according to claim 92, wherein $R_5$ is methyl.

94. 9-Deoxy-9-methylene-15-methyl-16-phenyl-17,18,19,20-trinor-5-oxa-$PGF_1$, tris(hydroxymethyl)aminomethane salt, a prostaglandin analog according to claim 93.

95. 9-Deoxy-9-methylene-15-methyl-16-phenyl-17,18,19,20-tetranor-5-oxa-$PGF_1$, a prostaglandin analog according to claim 93.

96. 9-Deoxy-9-methylene-15-methyl-16-phenyl-17,18,19,20-tetranor-5-oxa-$PGF_1$, a prostaglandin analog according to claim 93.

97. A prostaglandin analog according to claim 92, wherein $R_5$ is hydrogen.

98. 9-Deoxy-9-methylene-16-phenyl-17,18,19,20-tetranor-5-oxa-$PGF_1$, methyl ester, a prostaglandin analog according to claim 97.

99. 9-Deoxy-9-methylene-16-phenyl-17,18,19,20-tetranor-5-oxa-$PGF_1$, a prostaglandin analog according to claim 97.

* * * * *

UNITED STATES PATENT OFFICE
CERTIFICATE OF CORRECTION

Patent No. 4,159,385  Dated 26 June 1979

Inventor(s) Gordon L. Bundy

It is certified that error appears in the above-identified patent and that said Letters Patent are hereby corrected as shown below:

Column 2, lines 8-10, and lines 62-64, and Column 5, lines 1-4, "$R_2$ OH." should read -- $R_5$ OH. --

Column 2, line 17, "9-Deoxy-9-methylene-" should read -- 9-deoxy-9-methylene-5-oxa- --; line 20, "9-Deoxy-9-methylene-" should read -- 9-deoxy-9-methylene-5-oxa- --; line 56, "15-epi-16-methyl-" should read -- 15-epi-15-methyl- --;

Column 3, lines 34-35, "$PGF_1$, methyl ester," should read -- $PGF_1$, --;

Column 4, line 57, and Column 6, line 5, "$R_3$ $R_4$ is fluoro" should read -- $R_3$ and $R_4$ is fluoro --;

Signed and Sealed this

Second Day of September 1980

[SEAL]

Attest:

SIDNEY A. DIAMOND

*Attesting Officer*   *Commissioner of Patents and Trademarks*